United States Patent
Murphy et al.

(10) Patent No.: US 9,274,038 B2
(45) Date of Patent: Mar. 1, 2016

(54) APPARATUS AND METHOD FOR CONSTANT SHEAR RATE AND OSCILLATORY RHEOLOGY MEASUREMENTS

(75) Inventors: Robert J. Murphy, Kingwood, TX (US); Dale E. Jamison, Humble, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 741 days.

(21) Appl. No.: 13/403,701

(22) Filed: Feb. 23, 2012

(65) Prior Publication Data

US 2013/0226473 A1    Aug. 29, 2013

(51) Int. Cl.
*G01N 11/14*    (2006.01)

(52) U.S. Cl.
CPC ..................... *G01N 11/14* (2013.01)

(58) Field of Classification Search
CPC ..... G01N 11/10; G01N 11/14; G01N 11/142; G01N 11/165; G01N 2011/0026; G01N 2203/0025; G01N 2203/0094
USPC ........... 702/50, 33, 41–43, 66, 72–73, 75, 81, 702/84, 94, 100, 108, 112–113, 127, 145, 702/147, 150–151, 189; 73/53.01, 54.01, 73/54.14, 54.28, 54.31, 54.33–54.34, 73/54.37, 54.39
See application file for complete search history.

(56) References Cited

U.S. PATENT DOCUMENTS

| | | |
|---|---|---|
| 2,703,006 A | 3/1955 | Savins |
| 3,285,057 A | 11/1966 | De Zurik et al. |
| 3,343,405 A * | 9/1967 | Gilinson, Jr. et al. ........ 73/54.33 |
| 3,455,145 A | 7/1969 | Gustafsson |
| 3,803,903 A | 4/1974 | Lin |
| 3,864,961 A | 2/1975 | Cessna, Jr. |
| 3,986,388 A | 10/1976 | Stolzy |
| 4,005,599 A | 2/1977 | Schlatter et al. |
| 4,045,999 A | 9/1977 | Palmer |
| 4,062,225 A | 12/1977 | Murphy, Jr. et al. |
| 4,092,849 A | 6/1978 | Maxwell |
| 4,148,215 A | 4/1979 | Hofstetter, Jr. |
| 4,226,798 A | 10/1980 | Cowfer et al. |

(Continued)

FOREIGN PATENT DOCUMENTS

WO    WO-2013/126179    8/2013

OTHER PUBLICATIONS

Jimenez et al., A Novel Computerized Viscometer/Rheometer, Jan. 1994, Rev. Sci. Instrum. 65(1), pp. 229-241.*

(Continued)

*Primary Examiner* — Toan Le
(74) *Attorney, Agent, or Firm* — Krueger Iselin LLP; Scott H. Brown

(57) ABSTRACT

A rheometer instrument including a stationary frame, a sleeve suspended from the frame, a bob suspended within the sleeve, a cross-spring pivot suspending the bob from the stationary frame, and a force rebalance system for effecting the rotational displacement of the bob with a torque. The force rebalance system includes an arm attached to the movable portion of the cross-spring pivot, a rotational position sensor in close proximity to the arm for measuring the rotational displacement and angular frequency of the arm, and a force actuator positioned to apply force to the arm. The rheometer instrument may be used to calculate the rheological properties of Newtonian and non-Newtonian fluids.

24 Claims, 3 Drawing Sheets

(56) References Cited

U.S. PATENT DOCUMENTS

| | | | |
|---|---|---|---|
| 4,299,119 A | 11/1981 | Fitzgerald et al. | |
| 4,468,953 A | 9/1984 | Garritano | |
| 4,570,478 A | 2/1986 | Soong | |
| 4,571,988 A | 2/1986 | Murphy, Jr. | |
| 4,612,800 A | 9/1986 | Erian | |
| 4,643,020 A | 2/1987 | Heinz | |
| 4,779,627 A | 10/1988 | Kosasky | |
| 4,799,378 A | 1/1989 | Portman, Jr. et al. | |
| 4,864,849 A * | 9/1989 | Wright | 73/54.31 |
| 4,949,045 A | 8/1990 | Clark et al. | |
| 5,042,292 A | 8/1991 | Plint et al. | |
| 5,056,358 A | 10/1991 | Laskowski et al. | |
| 5,327,778 A | 7/1994 | Park | |
| 5,565,620 A | 10/1996 | Bohlin | |
| 5,708,197 A | 1/1998 | Todd et al. | |
| 6,073,483 A | 6/2000 | Nitecki et al. | |
| 6,257,051 B1 | 7/2001 | Boyle et al. | |
| 6,302,203 B1 | 10/2001 | Rayssiguier et al. | |
| 6,311,549 B1 | 11/2001 | Thundat et al. | |
| 6,412,338 B2 | 7/2002 | Boyle et al. | |
| 6,571,609 B1 | 6/2003 | Bi | |
| 6,584,833 B1 * | 7/2003 | Jamison et al. | 73/61.63 |
| 6,684,952 B2 | 2/2004 | Brockman et al. | |
| 6,727,827 B1 | 4/2004 | Edwards et al. | |
| 6,776,028 B1 | 8/2004 | Lukay | |
| 6,782,752 B2 | 8/2004 | Basir et al. | |
| 6,874,353 B2 | 4/2005 | Johnson et al. | |
| 6,938,464 B1 | 9/2005 | Bi | |
| 6,951,127 B1 | 10/2005 | Bi | |
| 6,962,086 B2 | 11/2005 | Prescott et al. | |
| 6,964,737 B2 | 11/2005 | Abu-Orf et al. | |
| 6,971,262 B1 | 12/2005 | Marchal et al. | |
| 6,990,850 B2 | 1/2006 | Taylor | |
| 6,993,972 B2 | 2/2006 | Basir et al. | |
| 6,997,045 B2 | 2/2006 | Wallevik et al. | |
| 7,007,546 B2 | 3/2006 | Andle | |
| 7,021,123 B2 | 4/2006 | Wallevik et al. | |
| 7,037,433 B2 | 5/2006 | Abu-Orf et al. | |
| 7,128,157 B2 | 10/2006 | Hoffman et al. | |
| 7,181,957 B2 | 2/2007 | Andle | |
| 7,204,129 B2 | 4/2007 | Basir et al. | |
| 7,441,442 B2 | 10/2008 | Morgan | |
| 7,526,946 B2 | 5/2009 | Wang | |
| 7,578,171 B2 | 8/2009 | Manneville | |
| 7,581,436 B2 | 9/2009 | Eskin et al. | |
| 7,603,897 B2 | 10/2009 | Gilbert et al. | |
| 7,701,229 B2 | 4/2010 | Murphy et al. | |
| 7,721,594 B2 | 5/2010 | Rogers et al. | |
| 7,721,595 B2 | 5/2010 | Rogers et al. | |
| 7,721,596 B2 | 5/2010 | Rogers et al. | |
| 7,830,161 B2 | 11/2010 | Murphy | |
| 7,926,326 B2 | 4/2011 | Franck et al. | |
| 7,942,036 B2 | 5/2011 | Wang | |
| 8,091,726 B2 | 1/2012 | Bradshaw et al. | |
| 2001/0042400 A1 | 11/2001 | Boyle et al. | |
| 2003/0140683 A1 | 7/2003 | Basir et al. | |
| 2003/0154772 A1 | 8/2003 | Jackson | |
| 2003/0183016 A1 | 10/2003 | Prescott et al. | |
| 2003/0192366 A1 * | 10/2003 | Taylor | 73/54.32 |
| 2004/0149019 A1 | 8/2004 | Johnson et al. | |
| 2004/0244489 A1 | 12/2004 | Basir et al. | |
| 2005/0056084 A1 | 3/2005 | Taylor | |
| 2005/0132782 A1 | 6/2005 | Wallevik et al. | |
| 2005/0132784 A1 | 6/2005 | Andle | |
| 2005/0138991 A1 | 6/2005 | Wallevik et al. | |
| 2005/0257629 A1 | 11/2005 | Gilbert et al. | |
| 2005/0284212 A1 | 12/2005 | Marchal et al. | |
| 2006/0096357 A1 | 5/2006 | Andle | |
| 2006/0123911 A1 | 6/2006 | Basir et al. | |
| 2007/0022802 A1 | 2/2007 | Rogers et al. | |
| 2007/0084272 A1 | 4/2007 | Wang | |
| 2007/0186625 A1 | 8/2007 | Rogers et al. | |
| 2007/0256507 A1 | 11/2007 | Morgan | |
| 2008/0034844 A1 | 2/2008 | Manneville | |
| 2008/0047328 A1 | 2/2008 | Wang | |
| 2008/0110246 A1 | 5/2008 | Old et al. | |
| 2008/0236254 A1 * | 10/2008 | Airey et al. | 73/54.23 |
| 2009/0056423 A1 | 3/2009 | Franck et al. | |
| 2009/0188304 A1 | 7/2009 | Eskin et al. | |
| 2009/0211343 A1 | 8/2009 | Zumbrunnen et al. | |
| 2010/0018294 A1 | 1/2010 | Tonmukayakul et al. | |
| 2010/0274504 A1 * | 10/2010 | Takahashi et al. | 702/50 |
| 2012/0017673 A1 | 1/2012 | Godager | |
| 2012/0024050 A1 | 2/2012 | Godager | |
| 2013/0110402 A1 | 5/2013 | Godager | |

OTHER PUBLICATIONS

Triantafillopoulos, N., Measurement of Fluid Rheology and Interpretation of Rheograms, Jan. 1988, Kaltec Scientific, Inc., 38 pp.*

PCT International Search Report and Written Opinion, dated May 31, 2013, Appl No. PCT/US2013/023065, "Apparatus and Method for Constant Shear Rate and Oscillatory Rheology Measurements", filed Jan. 25, 2013, 10 pgs.

AU First Examination Report, dated Aug. 12, 2014, Appl. No. 2013222825, "Apparatus and Method for Constant Shear Rate and Oscillatory Rheology Measurements," filed Jan. 25, 2013, 3 pgs.

AU Examination Report No. 2, dated Nov. 24, 2014, Appl No. 2013222825, "Apparatus and Method for Constant Shear Rate and Oscillatory Rheology Measurements ," Filed Jan. 25, 2013, 3 pgs.

PCT International Preliminary Report on Patentablility, dated Sep. 4, 2014, Appl No. PCT/US2013/023065, "Apparatus and Method for Constant Shear Rate and Oscillatory Rheology Measurements," Filed Jan. 25, 2013, 7 pgs.

* cited by examiner

APPARATUS AND METHOD FOR CONSTANT SHEAR RATE AND OSCILLATORY RHEOLOGY MEASUREMENTS

CROSS-REFERENCE TO RELATED APPLICATIONS

None.

BACKGROUND

When determining the rheology of a fluid, it is important to take the operating conditions of that fluid into consideration. Conditions such as temperature and pressure under which the fluid is utilized are important when measuring the rheological characteristics. As an example, many drilling fluids are subjected to temperatures above 400° F. and pressures greater than 10,000 psi in deep wellbores.

Conventional apparatuses for measuring the viscosity of Newtonian fluids include a cylindrical bob suspended within a concentric tubular sleeve for immersion in the fluid to be tested. The sleeve is rotated at a known velocity, causing the fluid in the annular space around the bob to drag on the suspended bob. The torque exerted on the bob provides a measure of the fluid viscosity. Typically, a stationary frame is used to suspend the bob and sleeve using ball or roller bearings. When used in harsh environments, these bearings may become pitted or gummed up, resulting in inaccurate viscosity measurements and, eventually, resulting in failure of the instrument.

In order to improve the reliability of the bearings, flexural or torsional bearings have been used. U.S. Pat. No. 4,571,988, titled "Apparatus and Method for Measuring Viscosity," discloses the use of a cross-spring pivot (CSP) as the flexural bearing, and is hereby incorporated by reference herein. A typical CSP is an arrangement of several flat springs configured so that when rotated for small angles, the springs bend so that the deflection appears to be about an axis. In some applications, the CSP axis is coaxial with the axis of the bob of the rheometer. Flexural pivots have many advantages. They have no sliding or rolling friction nor do they have tight clearances, so their rotational properties are very consistent. The CSP acting as a torsion spring and bearing support for the bob, permitting electronic measurement of the bob's rotational displacement to determine the fluid's shear stress. Though the device disclosed in U.S. Pat. No. 4,571,988 offers certain advantages with respect to accuracy and long-term reliability in harsh environments, it nevertheless lacks the ability to measure viscoelastic fluid properties such as the shear modulus. This ability would be useful for characterizing non-Newtonian fluids.

BRIEF DESCRIPTION OF THE DRAWINGS

Accordingly, there are disclosed in the drawings and the following description specific embodiments of apparatuses and methods that enable accurate shear rate and oscillatory rheology measurements. In the drawings.

Figure 1:
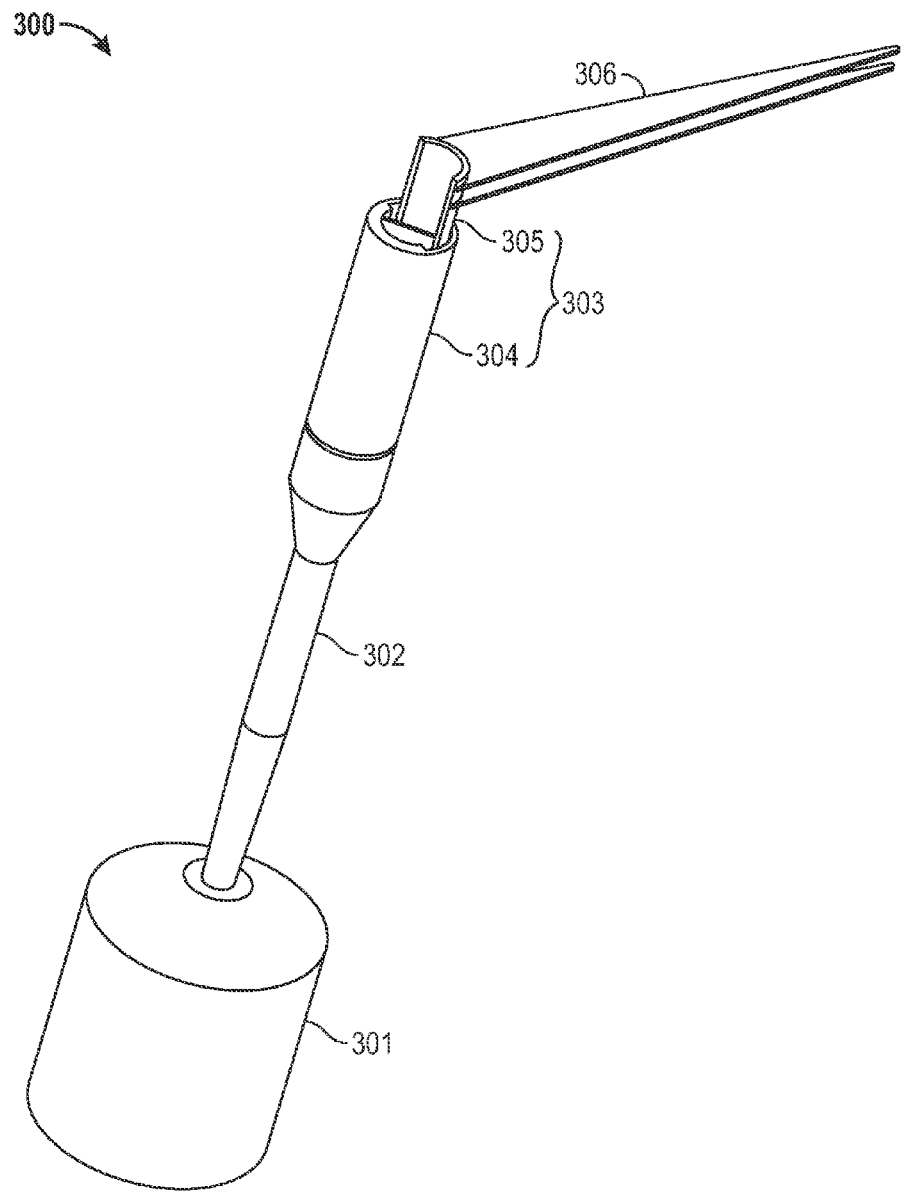
FIG. 1 is an isometric view of a crossed-spring pivot rheometer bob assembly.

It should be understood, however, that the specific embodiments given in the drawings and detailed description thereto do not limit the disclosure, but on the contrary, they provide the foundation for one of ordinary skill to discern the alternative forms, equivalents, and modifications that are encompassed with the given embodiments by the scope of the appended claims.

DETAILED DESCRIPTION

The present disclosure provides apparatuses and methods for measuring the viscoelastic properties of Newtonian and non-Newtonian fluids. Some embodiments are directed to methods including determining the shear stress of a fluid using a force rebalance technique to prevent the rotational displacement of the bob, e.g., by countering it with an electromagnetically generated opposing torque that just balances the torque from the bob. In the appropriate configuration, the current used to generate the balancing force is proportional to the shear stress.

Further embodiments provided by the present disclosure are directed to a force rebalance system (FRS) that may be used to rotate the bob and torsion assembly through small angles in a controlled manner from the normal balanced position so that other measurements can be made. Such embodiments may be useful for determining various properties of a gel, including its breaking point and the associated peak shear stress. The device may display the peak shear stress and/or other gel properties.

In another embodiment, the FRS can also be used to force the bob to oscillate for small displacements without rotating the outer cylinder (sleeve) of the rheometer. The phase difference between the driving force and the displacement can be used to make measurements of the viscoelastic properties of a fluid in the annular gap. The apparatus permits the measurement of the constant shear rate rheology with the prescribed API geometry and method. In a further embodiment, the oscillations could also be imposed on the bob while the sleeve is rotating at a constant shear rate so that both types of shear are imposed on the sample simultaneously.

Thus, the present disclosure provides novel apparatuses and methods to overcome the various problems of the prior art, thereby enabling an improved calculation of the viscoelastic properties of a fluid.

FIG. 1 is an isometric view of a crossed-spring pivot rheometer bob assembly 300. Assembly 300 comprises a bob 301, suspended by a bob shaft 302. The bob shaft 302 is attached to a cross-spring pivot 303. (A commercial example of the crossed-spring pivot is available from C-Flex Bearing Co., Inc. Frankfort, N.Y.) In another embodiment, the bob shaft 302 is an integral part of the crossed-spring pivot 303. The cross spring pivot 303 comprises a stationary portion 304 and a movable portion 305. A stand (not shown) anchors the stationary portion 304, while the bob shaft 302 is affixed to the movable portion 305 which rotates with the movement of the bob 301. In one embodiment, an arm 306 is attached to the movable portion 305, projecting radially from a point on the crossed-spring pivot 303. The far end of the arm 306 has a large displacement for small angular displacements of the bob shaft 302. The increased motion reduces the demands on a position sensor and force actuator (not shown) positioned in close proximity to the end of the arm.

Figure 2:
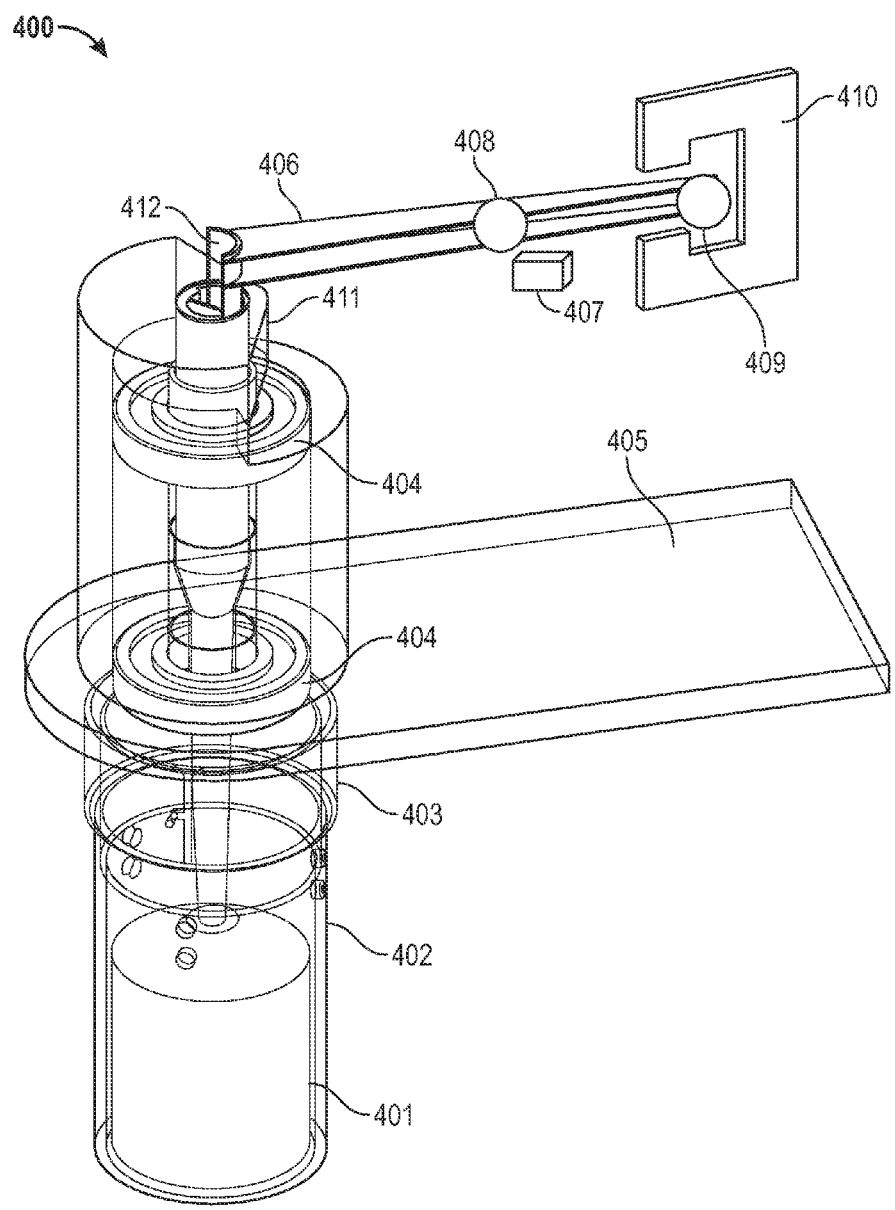
FIG. 2 is a partial schematic of an illustrative rheometer assembly.

FIG. 2 shows a partial schematic of an illustrative rheometer assembly 400. Rheometer assembly 400 comprises a bob 401 suspended in a sleeve 402. A main shaft 403 and main shaft bearings 404 are used to spin the sleeve 402 while allowing the bob 401 to stay suspended within the sleeve 402.

A frame 405 supports the sleeve assembly. In one embodiment, an arm 406 is attached to the movable portion 412 of a crossed-spring pivot 411, projecting radially from a point on the crossed-spring pivot 411. In some embodiments, a first magnet 408 is mounted on the arm 406 to enable position sensing by a Hall-effect sensor 407. A second magnet 409 may also be attached to the arm 406 near a force application device 410. In the illustrated embodiment, the force application device 410 does not physically contact the arm 406. In certain alternative embodiments, the force application device 410 physically contacts the arm 406. In certain embodiments, sleeve 402 is closed on the bottom. In another embodiment, sleeve 402 may be open on the bottom. If sleeve 402 closed on the bottom, fluid is placed in sleeve 402 and main shaft 403 may be rotated by a motor (not shown), thereby resulting in the sleeve 402 spinning. If sleeve 402 is open on the bottom, is the bob 401 and sleeve 402 can be immersed in the fluid. As the sleeve 402 spins, the bob 401 twists, causing the movable portion of crossed-spring pivot 411 to also twist. This twisting motion is counteracted by a force rebalance system comprising a coil 410, a force magnet 409 on the arm 406, a position magnet 408 on the arm 406, and a position sensor 407 positioned in close proximity to the position magnet 408. The force rebalance system will be detailed below.

Figure 3:
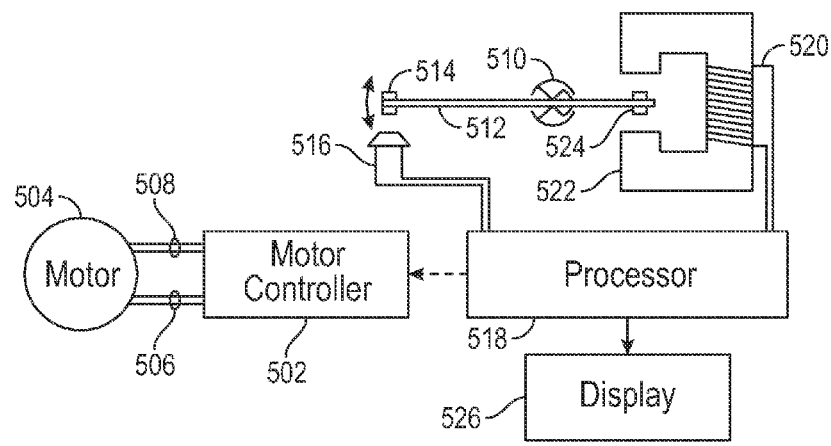
FIG. 3 is a block diagram illustrating functions of certain enhanced rheometer assembly components.

The present disclosure provides a force rebalance system to measure forces and induce a force on the arm of the force rebalance system. FIG. 3 shows a block diagram for an illustrative force rebalance system. Motor 504 rotates the sleeve of the rheometer. Motor controller 502 is an integrated circuit chip that controls motor 504. It may be programmed with the desired motor speed. The speed can be set manually or by processor 518 (e.g., if a sweep across a range of speeds is desired). Drive signal 506 can control the motor speed by varying the duty cycle of this signal. Speed sensor signal 508 is used to measure speed of motor 504 so that the motor controller can adjust the drive signal as necessary to ensure that the actual speed matches the programmed speed.

A bob is suspended from crossed-spring pivot 510. As the bob twists, sensor arm 512 turns with it. Sensor magnet 514 is utilized for sensing the bob position. A Hall-effect sensor 516 is used to measure the position of sensing magnet 514. Digital signal processor (DSP) 518 executes firmware that controls the operation of the rebalance system. Current through drive coil 520 creates a magnetic field. Core 522 directs the magnet field from drive coil 520 around force magnet 524. Force magnet 524 is used to counter the movement of sensor arm 512. As the DSP 518 detects movement of the position magnet 514, it adjusts the current through the drive coil as necessary to return the sensor arm 512 back to its original position. The necessary current level is indicative of the drag on the bob, enabling the DSP to derive the relevant fluid parameters and provide a digital output. Display 526 is used to display a digital output from the DSP 518.

Figure 4:
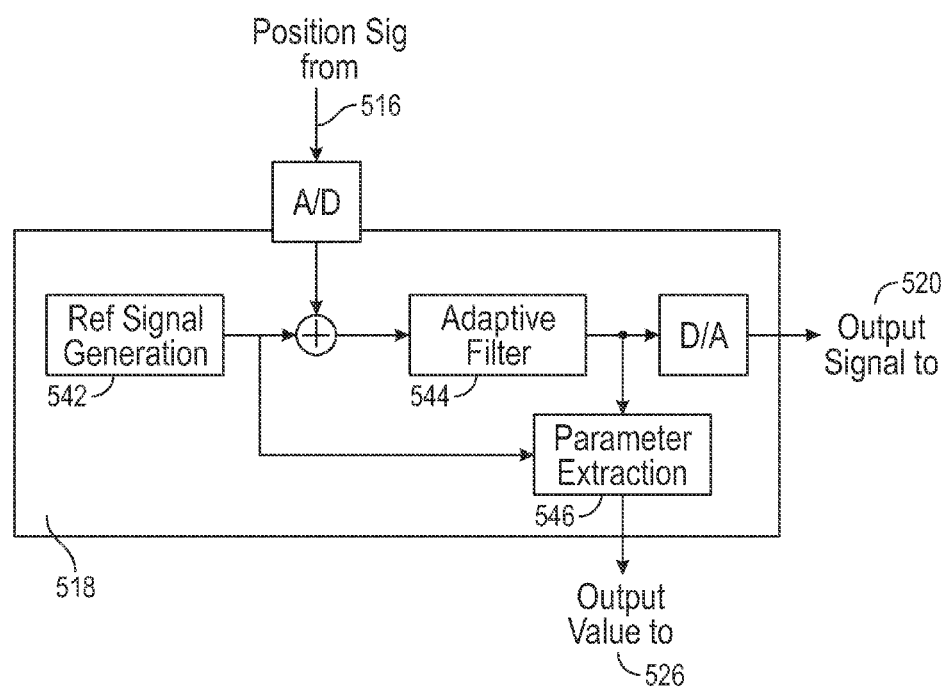
FIG. 4 is a block diagram illustrating digital signal processor functions implemented by an illustrative enhanced rheometer assembly.

FIG. 4 is a block diagram illustrating functions that may be implemented by the DSP 518. Reference signal generator 542 produces a sinusoidal wave of desired amplitude and frequency for oscillating measurements (which are explained further below). Reference signal generator 542 is set to zero for normal measurements. Adaptive filter 544 operates on the difference between reference signal 542 and the signal from position sensor 516 and produces an output signal designed to return the difference to zero. A digital to analog converter converts this output signal into a drive current for coil 520. Parameter extraction block 546, for normal measurements (reference signal is zero), averages the output signal amplitude and provides unit conversion if desired. When the motor speed is taken into account, the output signal is indicative of viscosity. For oscillating measurements, the parameter extraction block 546 measures the relative magnitude and the relative phase between a reference signal and an output signal.

Traditional Tests

A normal viscosity measurement is performed by moving one surface at a given velocity V relative to a second parallel surface. If the distance between the parallel surfaces is d, the fluid in the space between the surfaces is subjected to a shear rate of V/d. This shearing causes the fluid to exert a force F on the surfaces. This force divided by the area of one of the surfaces A is the shear stress F/A. The shear viscosity of the fluid is the ratio of the shear stress to the shear rate:

$$\eta = \frac{F/A}{V/d}.$$

If testing of oil field fluids is desired, the procedures are located in API RP-13B-1, Recommended Practice for Field Testing Water-based Drilling Fluids, the entire current version of which is incorporated by reference herein. In the traditional test for determining the viscosity of a fluid, the fluid is contained in the annular space between a bob and a sleeve. The sleeve is rotated at a constant rotational velocity. The rotation of the sleeve in the fluid produces a torque on the bob and the arm connected to the crossed-spring pivot. The force rebalance system of calculates the amount of force that is necessary to restore the arm to its resting position. This force is proportional to the viscosity of the fluid.

When measuring a gel according to the procedures in API RP-13B-1, if a slow rotation of the sleeve is used, i.e., 3 rpm, the initial gel strength is the maximum reading attained after starting the rotation. This is also known as the force at which the gel breaks.

Another variation of the gel test provided by the present disclosure is to rotate the bob throughout a small angle instead of constantly rotating the sleeve. The force rebalance system rotates the arm through a small angle from its normal position. The amount of rotation is that necessary to increase the shear stress at an equivalent rate obtained using the 3 rpm API procedure mentioned above. The breaking of the gel is detected by a rotational displacement sensor and the peak shear stress is measured using the force rebalance system.

Viscoelastic Measurements:

Oscillatory tests may be utilized to determine the viscoelastic properties of fluids. Rather than rotating a sleeve at a constant velocity around the bob, the oscillatory measurements may be accomplished by turning one slightly back and forth relative to the other. If the maximum amplitude of one surface's displacement relative to the other is X, the oscillatory shear strain is:

$$\gamma(t) = \frac{X}{d}\cos(\omega t). \tag{2}$$

For small displacements, this oscillatory shear strain produces an oscillatory shear stress:

$$\tau(t) = \frac{F}{A}\cos(\omega t + \delta) \tag{3}$$

where δ is a phase difference between the motion of the sleeve (or bob) and the force felt by the bob.

The complex shear modulus G* is defined with a real portion representing the in-phase relationship between oscillatory strain and stress, and an imaginary portion representing the quadrature-phase relationship:

$$G^* = G' + iG'' = \frac{F/A}{X/d}\cos(\delta) + i\frac{F/A}{X/d}\sin(\delta). \tag{4}$$

For purely elastic materials, the phase difference δ=0, whereas for purely viscous materials, δ=90°. The complex viscosity measurement can be derived from G*:

$$\eta^* = G^*/i\omega \tag{5}$$

with a real part equal to $$\eta = G''/\omega. \tag{6}$$

The complex shear modulus G* comprises a storage modulus represented by G', and a loss modulus represented by G". G' is related to the elastic behavior of the fluid and G" is related to the viscous behavior of the fluid. A loss factor is represented by tan(δ) and is defined as follows:

$$\tan(\delta) = G''/G' \tag{7}$$

This ratio is useful in determining the sol/gel transition point, or gel point of a fluid. When tan(δ)=1, the gel point has been reached. If tan(δ)>1, a liquid state exists, and if tan(δ)<1, the a gel state exists.

Rheological properties measured by the rheometer provided by the present disclosure include, but are not limited to, complex shear modulus G*, storage modulus G', a loss modulus G", complex viscosity η*, real portion of viscosity η', imaginary portion of viscosity η", phase shift angle δ, and loss factor tan(δ).

Dynamic Tests

There are two basic test modes in oscillatory tests. The first involves controlled shear deformation. In this test, strain γ(t) is introduced to the sample by inducing a deflection angle φ(t) on the crossed-spring pivot using a force on the force rebalance arm. Deflection angle φ(t) is represented by the following equation:

$$\phi(t) = \phi_A \cos(\omega t) \tag{8}$$

where $\phi_A$ is amplitude. The torque M(t) required to induce the deflection angle and the resulting phase shift angle δ are measured. Torque M(t) is represented by the following equation:

$$M(t) = M_A \cos(\omega t + \delta). \tag{9}$$

The torque M(t) is proportional to the shear stress τ(t), and the complex shear modulus G* may be calculated using Eq. (4).

The second test involves controlled shear stress. In this test, shear stress τ(t) is introduced to the sample by applying torque M(t) to the force rebalance arm and measuring the resulting deflection angle and phase shift. The complex shear modulus G* is then calculated using Eq. (4).

The measuring techniques will now be described in detail with reference to FIGS. 1-4. In a first example, the viscosity of a Newtonian fluid is determined by first immersing bob 401 in the fluid. The reference signal generator 542 is set to zero. Motor controller 502 is set to rotate motor 504 (and sleeve 402) at a certain speed using drive signal 506. As sleeve 402 rotates, bob 401 twists slightly causing arm 406 to also twist. Rotational position sensor 516 determines the position of position magnet 514. Processor 518 converts the signal to a digital signal and adaptive filter 544 operates on the difference between the signal from the reference signal generator 542 and the signal from rotational position sensor 516. An output signal is produced that should return the difference to zero, i.e., return arm 406 back to its resting position. The output signal is converted into a magnetic field by drive coil 520. Core 522 directs the magnetic field from coil 520 around force magnet 524, causing arm 406 to return to its resting position. The output signal amplitude is proportional to the viscosity, and this value may be displayed on display 526. One advantage of this system is that the output results in an accurate, digital viscosity, in part due to the additional distance traveled by arm 406 as opposed to placing a sensor on the movable portion 412 of crossed-spring pivot 411.

As another example, to measure the viscoelastic properties of a non-Newtonian fluid, bob 401 is immersed in the fluid and oscillating measurement techniques are used. The reference signal generator 542 is configured to produce a sinusoidal wave of desired amplitude and frequency for oscillating measurements. Motor controller 502 is set such that there is no rotation of motor 504. Because motor 504 does not rotate, sleeve 402 remains stationary. Rotational position sensor 516 determines the position of position magnet 514. Initially, position magnet 514 is stationary in its resting position. Processor 518 converts the signal to a digital signal and adaptive filter 544 operates on the difference between the signal from the reference signal generator 542 and the signal from rotational position sensor 516. An output signal is produced that should return the difference to zero, i.e., rotate arm 406 in an oscillating manner as set in reference signal generator 542. The output signal is converted into a magnetic field by drive coil 520. Core 522 directs the magnetic field from coil 520 around force magnet 524, causing arm 406 to rotate in an oscillating manner. Parameter extraction block 546 measures the relative magnitude and relative phase difference between the reference signal and the output signal. These values may be displayed on display 526 and used to further calculate rheological properties such as complex shear modulus G*, complex viscosity η*, and loss factor tan(δ).

If the fluid is a gel, the oscillation amplitude may be gradually ramped up, with monitoring of the forces exerted on the bob to determine the peak output signal representing the point at which a gel breaks, also known as the initial gel strength. The initial gel strength may be displayed on display 526. One advantage of this system is that the displacement of the arm is more controlled than a typical API gel measurement where the sleeve is rotated at a constant, slow rpm such as 3 rpm. Further, a more accurate, digital, peak shear stress value is obtained in part due to the additional distance traveled by arm 406 as opposed to placing a sensor on the movable portion 412 of crossed-spring pivot 411.

Another illustrative example is directed to measuring the viscoelastic properties of a non-Newtonian fluid using both constant shear and oscillating shear measurement techniques. Bob 401 is immersed in the fluid and oscillating measurement techniques are used in conjunction with a bias shear rate caused by rotation of the sleeve. To produce a bias shear rate, motor controller 502 is set to rotate motor 504 at a certain speed using drive signal 506. As sleeve 402 rotates, bob 401 rotates causing arm 406 to also rotate. To produce an oscillating shear, reference signal generator 542 is configured to produce a sinusoidal wave of desired amplitude and frequency for oscillating measurements. Rotational position sensor 516 determines the position of position magnet 514. Initially, position magnet 514 is stationary in its resting position. Processor 518 converts the signal to a digital signal and adaptive filter 544 operates on the difference between the signal from the reference signal generator 542 and the signal from rotational position sensor 516. An output signal is produced that should return the difference to zero, i.e., rotate arm 406 in an oscillating manner as set in reference signal generator 542. The output signal is converted into a magnetic field by drive coil 520. Core 522 directs the magnetic field from coil 520 around force magnet 524, causing arm 406 to rotate in an oscillating manner. Parameter extraction block 546 measures the relative magnitude and relative phase difference between the reference signal and the output signal. These values may be displayed on display 526 and used to further calculate rheological properties.

Numerous other modifications, equivalents, and alternatives, will become apparent to those skilled in the art once the above disclosure is fully appreciated. It is intended that the following claims be interpreted to embrace all such modifications, equivalents, and alternatives where applicable.

What is claimed is:

1. A rheometer that comprises:
   a rotatable sleeve that defines a cylindrical cavity;
   a cylindrical bob positioned within the cavity to define an annular space, the bob being supported by a cross-spring pivot that permits limited rotation of the bob;
   a force rebalance system that senses rotation of the bob and imposes a feedback force to counter any deviation of the bob from a reference point; and
   a processor that derives at least one viscoelastic parameter for a fluid in the annular space based at least in part on the feedback force.

2. The rheometer of claim 1, wherein the processor varies the reference point in a sinusoidal fashion and measures a relative amplitude and phase of the feedback force to derive the at least one viscoelastic parameter.

3. The rheometer of claim 2, wherein the processor accepts user input to vary at least one of an amplitude and angular frequency of the sinusoidal reference point variation.

4. The rheometer of claim 2, wherein the at least one viscoelastic parameter includes at least one parameter from the set consisting of: a storage modulus G', a loss modulus G", a real portion of viscosity $\eta'$, an imaginary portion of viscosity $\eta"$, and a phase shift angle $\delta$.

5. The rheometer of claim 4, wherein the at least one viscoelastic parameter further includes at least one of: a complex shear modulus G*, a complex viscosity $\eta^*$, and a loss factor tan($\delta$).

6. The rheometer of claim 1, wherein the reference point is held fixed while the rotatable sleeve rotates.

7. The rheometer of claim 6, wherein the rotatable sleeve turns at a constant rate during a measurement period.

8. The rheometer of claim 6, wherein the processor derives the at least one viscoelastic parameter based on the feedback force and a rotation rate of the sleeve.

9. The rheometer of claim 6, wherein the rotatable sleeve oscillates in a sinusoidal fashion.

10. The rheometer of claim 1, wherein the force rebalance system includes:
    an arm attached to a movable portion of the cross-spring pivot;
    a position sensor that measures a displacement of the arm; and
    an actuator that applies the feedback force to counter displacement of the arm from a reference position.

11. The rheometer of claim 10, wherein the actuator includes a drive coil that applies the feedback force by exerting a controllable magnetic force on said arm.

12. The rheometer of claim 1, further comprising a display coupled to the processor to output a digital value of the at least one viscoelastic parameter.

13. The rheometer of claim 1, wherein the feedback force is imposed without physical contact.

14. A method that comprises:
    subjecting, by a rheometer, a fluid in an annular space between a cylindrical bob and a sleeve to a shear strain, wherein the cylindrical bob is supported by at least one cross-spring pivot;
    sensing, by the rheometer, rotation of the bob;
    imposing, by the rheometer, a feedback force to counter any deviation of the bob from a reference point; and
    deriving, by the rheometer, at least one viscoelastic parameter for the fluid based at least in part on the feedback force.

15. The method of claim 14, further comprising:
    varying the reference point in a sinusoidal fashion; and
    measuring a relative amplitude and phase of the feedback force, wherein said deriving is based at least on the relative amplitude and phase.

16. The method of claim 15, further comprising varying at least one of an amplitude and an angular frequency of the sinusoidal reference point variation.

17. The method of claim 15, wherein the at least one viscoelastic parameter includes at least one parameter from the set consisting of: a storage modulus G', a loss modulus G", a real portion of viscosity $\eta'$, an imaginary portion of viscosity $\eta"$, and a phase shift angle $\delta$.

18. The method of claim 17, wherein the at least one viscoelastic parameter further includes at least one of: a complex shear modulus G*, a complex viscosity $\eta^*$, and a loss factor tan($\delta$).

19. The method of claim 14, wherein said subjecting is performed by rotating the sleeve while holding the reference point fixed.

20. The method of claim 19, wherein the rotatable sleeve turns at a constant rate during a measurement period.

21. The method of claim 19, wherein the rotatable sleeve oscillates in a sinusoidal fashion.

22. The method of claim 14, wherein the feedback force is imposed without physical contact.

23. The method of claim 14, wherein the fluid is a gel and the bob is rotated by the force rebalance system to increase shear stress on the gel to a point where the gel breaks.

24. The method of claim 23, wherein the viscoelastic parameter is the gel break point.

* * * * *